United States Patent [19]

Iwasaki

[11] Patent Number: 5,627,166
[45] Date of Patent: May 6, 1997

[54] ACTIVATOR FOR ACARACIDE

[75] Inventor: Tetsuji Iwasaki, Wakayama, Japan

[73] Assignee: Kao Corporation, Tokyo, Japan

[21] Appl. No.: 478,266

[22] Filed: Jun. 7, 1995

Related U.S. Application Data

[62] Division of Ser. No. 451,187, May 26, 1995, abandoned, which is a division of Ser. No. 166,597, Dec. 13, 1993, abandoned, which is a continuation of Ser. No. 418,903, Oct. 5, 1989, abandoned, which is a continuation of Ser. No. 139,720, Dec. 30, 1987, abandoned, which is a division of Ser. No. 42,545, Apr. 24, 1987, abandoned, which is a continuation of Ser. No. 725,028, Apr. 19, 1985, abandoned.

[30] Foreign Application Priority Data

Apr. 23, 1984 [JP] Japan .................................. 59-081538

[51] Int. Cl.$^6$ .............................. A01N 57/26; A01N 31/04
[52] U.S. Cl. .............................................. 514/78; 514/726
[58] Field of Search ........................................ 514/78, 726

[56] References Cited

U.S. PATENT DOCUMENTS 4,313,847 2/1982 Chasin et al. ............................ 252/356

OTHER PUBLICATIONS

Schwartz et al 1958, Surface Active Agents & Detergents, vol. II, Interscience New York pp. 649–660.

*Primary Examiner*—Russell Travers
*Attorney, Agent, or Firm*—Flynn, Thiel, Boutell & Tanis, P.C.

[57] ABSTRACT

A acaricidal composition comprising an effective amount of a acaricide and an effective amount of a biocide activator selected from the group consisting of an alkyl phosphate, an alkenyl phosphate, a hydroxyalkyl phosphate, a polyoxyalkylene alkyl ether phosphate, a salt thereof, a polyoxyalkylene alkenyl ether phosphate, a salt thereof, a polyoxyalkylene hydroxyalkyl ether phosphate and a salt thereof.

17 Claims, No Drawings

ACTIVATOR FOR ACARACIDE

This is a division of Ser. No. 08/451,187 now abandoned, filed May 26, 1995, which is a division of Ser. No. 08/166 597, now abandoned filed Dec. 13, 1993, which is a continuation of Ser. No. 07/418,903, now abandoned filed Oct. 5, 1989, which is a continuation of Ser. No. 07/139 720, now abandoned filed Dec. 30, 1987, which is a division of Ser. No. 07/042 545, now abandoned filed Apr. 24, 1987, which is a continuation of Ser. No. 07/725 028, now abandoned filed Apr. 19, 1985.

The present invention relates to an activator for biocides.

Biocides such as insecticides, germicides, herbicides and plant growth regulators have been used in the form of an emulsion, wettable powder, flowable product, grains or powder.

The physical properties of the biocides have been modified variously so as to exhibit the activity of the active ingredient sufficiently. However, it has been impossible to further increase the effects of the biocide.

It is quite significant to further increase the effects of known biocides, since the development of new biocides is now very difficult.

After intensive investigations, the inventors have found that specified compounds are effective in further activating various biocides. The present invention has been completed no the basis of this finding.

The invention provides a biocidal composition which comprises an effective amount of a biocide and an effective amount of a biocide activator selected from the group consisting of an alkyl phosphate, an alkenyl phosphate, a hydroxyalkyl phosphate, a polyoxyalkylene alkyl ether phosphate, a salt thereof, a polyoxyalkylene alkenyl ether phosphate, a salt thereof, a polyoxyalkylene hydroxyalkyl ether phosphate and a salt thereof. The invention may be provided in the form of an emulsion concentrate which comprises 10 to 70 weight percent of the biocide and 10 to 50 weight percent of the biocide activator, 3 to 20 weight percent of an emulsifier and 10 to 50 percent weight of an organic solvent, or a dilute composition which comprises 100 to 5,000 ppm of the biocide, 200 to 10,000 ppm, preferably 500 to 5,000 ppm, of the biocide activator and a carrier for dilution. The diluent composition is usually prepared just in advance to use thereof.

The alkyl phosphates, polyoxyalkylene alkyl ether phosphates and salts of them according to the present invention may be prepared by known processes. For example, they are obtained by reacting an alcohol (if necessary, after addition of an alkylene oxide thereto) with phosphorus pentoxide and, if necessary, neutralizing the reaction product.

The starting alcohol has 1 to 22 carbon atoms and contains a straight-chain or branched alkyl group, an alkenyl group having double bond(s) or hydroxyl group(s) in the chain or a hydroxyalkyl group. The alcohol contains preferably 4 to 18 carbon atoms, 0 to 4, preferably 0 to 2 double bonds and 0 to 4, preferably 0 to 2, hydroxyl groups. The alcohols include, for example, butanol, 2-ethylhexanol, lauryl alcohol, stearyl alcohol and oleyl alcohol.

The alkylene oxides to be added to the alcohol to form a polyoxyalkylene chain include ethylene oxide, propylene oxide and butylene oxide. They may be used either alone or in the form of block or random adducts of two or more of them. The mol number of addition is 1 to 100, preferably 1 to 50.

The addition reaction may be carried out by a known process by, for example, introducing an alkylene oxide into an alcohol in the presence of an acid or alkaline catalyst at 50° to 200° C. under 1 to 5 kg/cm$^2$. The alcohol or polyoxyalkylene alkyl ether may be phosphated by various processes. For example, 3 mol of the alcohol or polyoxyalkylene alkyl ether is reacted with 1 mol of phosphorus pentoxide at 80° to 100° C. for about 6 h to obtain a corresponding phosphate easily. The obtained alkyl phosphate or polyoxyalkylene alkyl ether phosphate is a mixture of a monoester and a diester in substantially equal amounts. Though excellent effects are exhibited when the activator for biocides of the present invention is any of the monoester and the diester, particularly excellent effects are obtained when it is a monoester, particularly a polyoxyalkylene alkyl ether/phosphoric monoester or a salt thereof.

When said phosphate is neutralized with a base, a corresponding polyoxyalkylene alkyl ether phosphate salt is obtained. This ester salt also has an excellent activating effect. The salts include alkali metal, alkaline earth metal, monoethanolamine, diethanolamine, triethanolamine and ammonium salts.

When the activator for biocides of the present invention is used in combination with a biocide, the effect of the biocides can be increased 2 or 3-folds irrespective of the variety of the biocide.

The activator of the present invention is used in an amount of 0.05 to 20, preferably 1 to 15 parts by weight per part by weight of the biocide.

The biocide may be in the form of any of an emulsion, flowable product, wettable powder and powder. Therefore, other additives such as an emulsifying agent, dispersant and carrier may be incorporated therein according to the form of the biocide.

The activator of the present invention may be used by incorporating the same into the biocide of the above-mentioned form according to the formulation or by applying the same to a subject in combination with the biocide at the time of the application of the biocide in a diluted form. The activating effect according to the invention can be obtained in both cases.

Though the mechanism of such a remarkable activation of the biocide by the activator of the present invention has not been fully elucidated yet, it may be presumed that the activator for biocide of the present invention has an extremely high power of solubilizing the biocide irrespective of the structure of the biocide and, therefore, the biocide is finely divided and the penetration thereof through the surfaces of plants or into insects and germs is accelerated.

The present invention provides also a biocidal process characterized by spraying an emulsion (or dispersion) of a biocide containing the above-described activator.

Examples of the biocides which are activated by the activator of the present invention will be given below, which by no means limit the biocides to be activated according to the present invention. The activator of the present invention can be used safely without damaging the farm products. The insecticides include pyrethroid insecticides such as Fenvalerate [α-cyano-3-phenoxybenzyl-2-(4-chlorophenyl)-3-methylvalerate] and Pyrethroid [cyano(4-fluoro-3-phenoxyphenylmethyl-3-(2, 2-dichloroethenyl)-2,2-dimethylcyclopropanecarboxylate]; organophosphorus insecticides such as DDVP (2,2-dichlorovinyldimethyl phosphate), Sumithion (dimethyl-4-nitro-m-tolylphosphorothionate), Malathon {S-[1,2-bis (ethoxycarbonyl)ethyl]dimethylphosphorothiol thionate}, Dimethoate [dimethyl-S-(N-methylcarbamoylmethyl) phosphorothiol thionate), Elsan {S-[α-(ethoxycarbonyl) benzyl]dimethylphosphorothiol thionate) and Baycid [0,0-dimethyl-0-(3-methyl-4-methylmercaptophenyl)

thiophosphate]; carbamate insecticides such as Bassa (0-butylphenyl methylcarbamate), MTMC (m-tolyl methylcarbamate), Meobal (3,4-dimethylphenyl-N-methylcarbamate), NAC (1-maphthyl-N-methylcarbamate); as well as Methomyl {methyl-N[(methylcarbamoyl)oxy] thioacetimide} and Cartap {1,3-bis(carbamoylthio)-2-(N,N-dimethylamino) propane hydrochloride].

Examples of acaricides include Smite {2-[2-(p-tart-butylphenoxy) isopropoxy]isopropyl-2-chloroethyl sulfide}, Acricid (2,4-dinitro-6-sec-butylphenyl dimethylacrylate), Chlormit (isopropyl 4,4-dichlorobenzylate), Acar (ethyl 4,4-dichlorobenzylate), Kelthane [1,1-bis(p-chlorophenyl)-2,2,2-trichloroethanol], Citrazon (ethyl 0-benzoyl-3-chloro-2,6-dimethoxybenzohydroxymate), Plictran (tricyclohexyltin hydroxide) and Omite [2-(p-tert-butylphenoxy)cyclohexyl-2-propinyl sulfite].

Examples of the germicides include organosulfur germicides such as Dithane (zinc ethylenebisdithiocarbamate), maneb (manganese ethylenebisdithiocarbamate), thiuram [bis(dimethylthiocarbamoyl) disulfide], Benlate [methyl 1-(butylcarbamoyl)-2-benzimidazole carbamate], Difolatan (N-tetrachloroethylthio-4-cyclohexane-1,2-dicarboxyimide), Daconol (tetrachloroisophthalonitrile), Pansoil (5-ethoxy-3-trichloromethyl-1,2,4-thiadiazole), Thiophanate-methyl[1,2-bis(3-methoxycarbonyl-2-thioureido) benzene], Rabcide (4,5,6,7-tetrachlorophthaloid), Kitazin P (0,0-diisopropyl-S-benzyl phosphorothioate), Hinosan (0-ethyl-S,S-diphenyldithiophosphate) and Propenazol (3-allyloxy-1,2-benzothiazole 1,1-dioxide).

Examples of the herbicides include Stam (3,4-dichloropropionanilide), Saturn [S-(4-chlorobenzyl) N,N-diethylthiolcarbamate), Lasso (2-chloro-2',6'-diethyl-N-(methoxymethyl) acetanilide), Glyphosate [N-(phosphonomethyl)glycine isopropylamine salt], DCMU [3-(3,4-dichlorophenyl)-1,1-dimethylurea) and Gramoxone (1,1'-dimethyl-4,4'-dipyridium dichloride].

Examples of the plant growth regulating agents include MH (maleic acid hydrazide) and Ethrel (2-chloroethylphosphonic acid).

EXAMPLES AND EFFECTS

The following examples will further illustrate the activators for biocides of the present invention.

Example 1

A compound of the present invention was dissolved in a commercially available herbicide (Karmex wettable powder, Simazine wettable powder, Paraquat solution or Glyphosphate solution) to obtain a 0.2% solution. 10 ml of the solution was sprayed to each pot of crabgrass (a weed of Graminese) which had been grown uniformly. The herbicidal effects of them were compared with one another. The crabgrasses used were in a three- or four-foliate period having a height of about 10 cm. Each pot had 25 crabgrasses. The dilution rate of said Karmex wettable powder. Simazine wettable powder, Paraquat solution or Glyphosphate solution was 1/300. The herbicidal rate was determined by weighing the above-the-ground parts of the crabgrasses 10 days after the spraying and the results were represented by percentage based on the weight of untreated grasses. The results are shown in Table 1.

TABLE 1

| | Herbicidal rate (%) | | | |
|---|---|---|---|---|
| | Karmex wettable powder | Simazine wettable powder | Paraquat solution | Glyphosate solution |
| Activator of the present invention | | | | |
| POE(3) 2-ethylhexyl phosphate | 84.0 | 67.2 | 98.2 | 100 |
| POE(3) POP(5) 2-ethylhexyl phosphate | 80.8 | 68.5 | 99.1 | 100 |
| POE(3) POP(5) 2-ethylhexyl phosphate/ diethanolamine | 81.0 | 68.9 | 99.0 | 100 |
| POE(10) octyl phosphate | 78.4 | 70.5 | 100 | 100 |
| Potassium POE(10) octyl phosphate | 79.8 | 72.4 | 100 | 100 |
| POE(30) lauryl phosphate | 85.7 | 80.2 | 100 | 100 |
| POE(30) lauryl phosphate monoethanolamine | 86.0 | 81.5 | 100 | 100 |
| POE(60) POB(10) palmityl phosphate | 78.8 | 82.4 | 100 | 100 |
| Sodium POE(60) POB (10) palmityl phosphate | 72.1 | 82.0 | 100 | 100 |
| POE(25) POP(10) oleyl phosphate | 89.1 | 89.5 | 100 | 100 |
| Ammonium POE(25) POP(10) oleyl phosphate | 89.5 | 87.8 | 100 | 100 |
| POE(80) linoleyl phosphate | 88.4 | 88.1 | 100 | 100 |
| Calcium POE(80) linoleyl phosphate | 89.4 | 89.9 | 100 | 100 |
| 2-Ethylhexyl phosphate | 69.0 | 60.0 | 95.0 | 97.2 |
| Lauryl phosphate | 70.1 | 72.5 | 90.4 | 90.0 |
| Oleyl phosphate | 75.2 | 79.0 | 94.0 | 92.0 |
| No activator used Comparative | 21.0 | 18.4 | 64.2 | 68.4 |
| POE(3) 2-ethylhexyl ether | 51.2 | 42.8 | 69.0 | 70.0 |
| POE(10) octyl ether | 49.0 | 40.4 | 72.0 | 78.4 |
| POE(30) lauryl ether | 52.5 | 54.5 | 72.0 | 80.5 |
| POE(25) POP(10) oleyl ether | 57.5 | 52.8 | 79.5 | 75.5 |
| POE(60) POB(10) palmityl ether | 45.4 | 42.1 | 72.8 | 75.6 |
| POE(80) linoleyl ether | 60.5 | 55.2 | 79.2 | 80.0 |

Note:
Symbols POE, POP and POB represent polyoxyethylene, polyoxypropylene and polyoxybutylene, respectively. The numerals in the parentheses represent the mol number of addition.

Example 2

Third-instar larvae of plant hoppers were cultured and the insecticidal effects of insecticides thereon were examined by the leaf dipping method 3 repetition. Each group consisted of 10 larvae. The insecticidal effects were compared with those in an untreated group 24 h after the treatment. The results are shown in Table 2.

The insecticides used were a Sumithion emulsion and a Malathon emulsion each diluted to a concentration of 1/2000. The concentration of the activator of the present invention was controlled to 0.1% based on the diluted emulsion.

TABLE 2

|  | Insecticidal rate (%) | |
| --- | --- | --- |
|  | 50% Sumithion emulsion | 50% Malathon emulsion |
| Activator of the present invention | | |
| POE(3) 2-ethylhexyl phosphate | 84.5 | 80.5 |
| POE(3) POP(5) 2-ethylhexyl phosphate | 82.5 | 78.4 |
| POE(3) POP(5) 2-ethylhexyl phosphate diethanolamine | 82.5 | 78.5 |
| POE(10) octyl phosphate | 80.5 | 80.0 |
| Potassium POE(10) octyl phosphate | 81.2 | 78.9 |
| POE(30) lauryl phosphate | 86.4 | 82.4 |
| POE(30) lauryl phosphate monoethanolamine | 86.9 | 86.7 |
| POE(60) POB(10) palmityl phosphate | 78.5 | 80.0 |
| Sodium POE(60) POB(10) palmityl phosphate | 82.4 | 81.5 |
| POE(25) POP(10) oleyl phosphate | 90.1 | 94.6 |
| Ammonium POE(25) POP(10) oleyl phosphate | 86.5 | 90.0 |
| POE(80) linoleyl phosphate | 89.5 | 92.1 |
| Calcium POE(80) linoleyl phosphate | 90.5 | 92.6 |
| 2-Ethylhexyl phosphate | 68.2 | 60.0 |
| Lauryl phosphate | 75.1 | 72.0 |
| Linoleyl phosphate | 85.1 | 80.0 |
| No activator used | 49.0 | 40.0 |
| Comparative | | |
| POE(3) 2-ethylhexyl ether | 52.5 | 41.5 |
| POE(10) octyl ether | 55.0 | 40.5 |
| POE(30) lauryl ether | 55.5 | 42.8 |
| POE(25) POP(10) oleyl ether | 49.0 | 39.5 |
| POE(60) POB(10) palmityl ether | 50.5 | 40.0 |
| POE(80) linoleyl ether | 56.0 | 45.2 |

Example 3

Male imagines of two-spotted red spider were applied to leaf disks of kidney beans in three replications. Each group consisted of 30 imagines. After the culture at 25° C. for 24 h. 0.2 ml per each group of a test sample was sprayed by the chromatospray method. The insecticidal rate was determined by comparison with the results of an untreated group 24 h after the treatment. The acaricides used were Amitraz emulsion and Osadan wettable powder diluted to a concentration of 1/2000. The concentration of the activator of the present invention was controlled to 0.1% based on the diluted product. The results are shown in Table 3.

TABLE 3

|  | Insecticidal rate (%) | |
| --- | --- | --- |
|  | 20% Amitraz emulsion | 20% Osadan emulsion |
| Activator of the present invention | | |
| POE(3) 2-ethylhexyl phosphate | 92.5 | 100 |
| POE(3) POP(5) 2-ethylhexyl phosphate | 96.0 | 100 |
| POE(3) POP(5) 2-ethylhexyl phosphate diethanolamine | 96.0 | 100 |
| PIE(10) octyl phosphate | 98.0 | 95.4 |

TABLE 3-continued

|  | Insecticidal rate (%) | |
| --- | --- | --- |
|  | 20% Amitraz emulsion | 20% Osadan emulsion |
| Potassium POE(10) octyl phosphate | 98.5 | 99.0 |
| POE(30) lauryl phosphate | 97.5 | 100 |
| POE(30) lauryl phosphate monoethanolamine | 90.0 | 100 |
| POE(60) POB(10) palmityl phosphate | 95.0 | 100 |
| Sodium POE(60) palmityl phosphate | 92.5 | 100 |
| POE(25) POP(10) oleyl phosphate | 100 | 100 |
| Ammonium POE(25) POP(10) oleyl phosphate | 100 | 100 |
| POE(80) linoleyl phosphate | 100 | 100 |
| Calcium POE(80) linoleyl phosphate | 100 | 100 |
| No activator used | 58.2 | 64.2 |

It is apparent from Examples 1 to 3 that the activators of the present invention have an excellent activating effect. In addition, each composition as prepared in Examples 1 to 3 was diluted with water. The obtained dilute one was effective to improve the biocide activity. Each component content in the dilute compositions is given below.

| In the compositions of Example 1 | |
| --- | --- |
| activator | 2000 ppm |
| Karmex | 1660 |
| Simazine | 1660 |
| Paraquat | 800 |
| Round-Up | 660 |
| In the compositions of Example 2 | |
| activator | 1000 ppm |
| Sumithion | 250 |
| Malathon | 250 |
| In the compositions of Example 3 | |
| activator | 1000 ppm |
| Dani-Cut | 100 |
| Osadan | 225 |

The embodiments of the invention in which an exclusive property or privilege is claimed are defined as follows:

1. An agricultural acaricidal composition which consists essentially of an effective amount of an agricultural chemical acaricide and an effective amount of a substance for increasing the acaricidal rate of said acaricide, said acaricide being selected from the group consisting of 2-(p-tert-butylphenoxy) cyclohexyl-2-propinyl sulfite and 1,1-bis(p-chlorophenyl)-2,2,2-trichloroethanol; and said substance being selected from the group consisting of an alkyl phosphate, an alkenyl phosphate, a hydroxy alkyl phosphate, a polyoxyalkylene alkyl ether phosphate, a polyoxyalkylene alkenyl ether phosphate, a polyoxyalkylene hydroxyalkyl ether phosphate and salts thereof, said substance having from 1 to 22 carbon atoms in the alkyl or alkenyl group thereof, the weight ratio of said substance/said acaricide being in the range of 1/1 to 15/1.

2. A composition as claimed in claim 1, in which said substance has 1 to 100 oxyalkylene units and the alkylene group therein has 2, 3 or 4 carbon atoms.

3. An acaricidal composition as claimed in claim 1, in which each of said phosphates is a monoester of phosphoric acid.

4. An acaricidal composition as claimed in claim 1, in which said substance is a polyoxyalkylene alkyl ether phosphate monoester, a salt thereof, a polyoxyalkylene alkenyl ether phosphate monoester, or a salt thereof, said alkyl and alkenyl groups having 4 to 18 carbon atoms and the number of said oxyalkylene units being from 1 to 50.

5. An acaricidal composition as claimed in claim 1, wherein said alkyl is selected from the group consisting of lauryl and palmityl, and said alkenyl is selected from the group consisting of oleyl, 2-ethylhexyl and linoleyl.

6. A method of controlling acaricides which comprises applying to a zone containing acaricides an acaricidally effective amount of a composition as defined in claim 1.

7. A composition as claimed in claim 1, in which said substance is anionic and is selected from the group consisting of a polyoxyalkylene alkylether phosphate, a polyoxyalkylene alkenyl ether phosphate, and salts thereof.

8. A composition as claimed in claim 1, in which said substance is selected from the group consisting of an alkyl phosphate and an alkenyl phosphate.

9. A composition as claimed in claim 1, in which said substance is selected from the group consisting of a hydroxyalkyl phosphate and polyoxyalkylene hydroxyalkyl ether phosphate.

10. An acaricidal composition as claimed in claim 2, in which said acaricide is 2-(p-tert-butylphenoxy) cyclohexyl-2-propinyl sulfite and the substance is a polyoxyalkylene alkyl ether phosphoric monoester or a salt thereof.

11. An acaricidal composition as claimed in claim 2, in which said acaricide is 1,1-bis(p-chlorophenyl)-2,2,2-trichloroethanol and the substance is a polyoxyalkylene alkyl ether phosphoric monoester or a salt thereof.

12. A composition as claimed in claim 4, in which the acaricide is 2-(p-tert-butylphenoxy) cyclohexyl-2-propinylsulfite and said substance is selected from the group consisting of POE(3)POP(5)2-ethylhexyl ether phosphate, POE(3)POP(5)2-ethylhexyl ether phosphate diethanolamine, monoethalamine POE(30)lauryl ether phosphate, sodium POE(60)POB(10)palmityl ether phosphate, sodium POE(25)POP(10)oleyl ether phosphate, potassium POE(80)linoleyl ether phosphate, POE(6)POP(2) lauryl ether phosphate and triethanolamine POE(4)C16 Guerbet ether phosphate.

13. A composition as claimed in claim 4, in which the acaricide is 1,1-bis(p-chlorophenyl)-2,2,2-trichloroethanol and said substance is selected from the group consisting of potassium POE(10)octyl ether phosphate, sodium POE(60)POB(10)palmityl ether phosphate, sodium POE(25)POP(10)oleyl ether phosphate, potassium POE(80)linoleyl ether phosphate and triethanolamine POE(4)C16 Guerbet ether phosphate.

14. An agricultural acaricidal composition which consists essentially of an effective amount of an agricultural chemical acaricide, an effective amount of a substance for increasing the acaricidal rate of said acaricide and an inert carrier, said acaricide being selected from the group consisting of 2-(p-tert-butylphenoxy) cyclohexyl-2-propinyl sulfite and 1,1-bis(p-chlorophenyl)-2, 2,2-trichloroethanol; and said substance being selected from the group consisting of an alkyl phosphate, an alkenyl phosphate, a hydroxyalkyl phosphate, a polyoxyalkylene alkyl ether phosphate, a polyoxyalkylene alkenyl ether phosphate, a polyoxyalkylene hydroxyalkyl ether phosphate and salts thereof, said substance having from 1 to 22 carbon atoms in the alkyl or alkenyl group thereof, the weight ratio of said substance/said acaricide being in the range of 1/1 to 15/1.

15. An acaricidal composition as claimed in claim 14, which comprises from 100 to 5,000 ppm, based on the composition, of said acaricide, from 200 to 10,000 ppm, based on the composition, of said substance and the balance is an inert carrier.

16. An acaricidal composition as claimed in claim 14, in which said acaricide is 2-(p-tert-butylphenoxy) cyclohexyl-2-propinyl sulfite and the substance is a polyoxyalkylene alkyl ether phosphoric monoester or a salt thereof.

17. An acaricidal composition as claimed in claim 14, in which said acaricide is 1,1-bis(p-chlorophenyl)-2,2,2-trichloroethanol and the substance is a polyoxyalkylene alkyl ether phosphoric monoester or a salt thereof.

* * * * *